(12) United States Patent
Anderson

(10) Patent No.: US 6,390,966 B2
(45) Date of Patent: May 21, 2002

(54) METHOD FOR MAKING DENSITY GRADIENTS

(75) Inventor: Norman G. Anderson, Rockville, MD (US)

(73) Assignee: Large Scale Proteomics Corporation, Vacaville, CA (US)

( * ) Notice: Subject to any disclaimer, the term of this patent is extended or adjusted under 35 U.S.C. 154(b) by 0 days.

(21) Appl. No.: 09/836,345

(22) Filed: Apr. 18, 2001

Related U.S. Application Data

(62) Division of application No. 09/551,314, filed on Apr. 18, 2000, now abandoned.

(51) Int. Cl.$^7$ ................................................ B04B 11/04

(52) U.S. Cl. ........................................................ 494/37

(58) Field of Search ..................... 494/37, 85; 210/513, 210/514, 516, 518

(56) References Cited

U.S. PATENT DOCUMENTS

| | | | |
|---|---|---|---|
| 963,500 A | | 7/1910 | Beechel |
| 967,372 A | | 8/1910 | Hackett et al. |
| 2,550,589 A | | 4/1951 | Orme, Jr. |
| 3,185,189 A | | 5/1965 | Reid |
| 3,909,419 A | * | 9/1975 | Ayers |
| 4,001,122 A | * | 1/1977 | Griffin |
| 4,088,582 A | * | 5/1978 | Murty et al. |
| 4,346,608 A | | 8/1982 | Oelnick et al. |
| 4,636,361 A | | 1/1987 | Marian et al. |
| 4,917,801 A | | 4/1990 | Luderer et al. |
| 5,163,488 A | | 11/1992 | Basch |
| 5,178,091 A | | 1/1993 | Griller et al. |
| 5,314,074 A | * | 5/1994 | Inbar et al. |

OTHER PUBLICATIONS

Anderson et al., Anayltical Techniques for Cell Fractions: VII. A Simple Gradient–Forming Apparatus. *Anal Biochem* (1967) 21:259–265.

Atherton et al., Chromatography and Zonal Centrifugation: Predictions of the Optimum Initial Chamber Compositions of a Multichambered Concentration and Density Gradient Device. *Anal Biochem* (1972) 49:326–335.

Ayad et al., A Simple Method for the Production of Accurate Linear Gradients Using a Constant–Speed Peristaltic Pump. *Anal Biochem* (1968) 22:533–535.

Birnie et al., A Simple Density–Gradient Engine for Loading Large–Capacity Zonal Ultracentrifuge Rotors. *Anal Biochem* (1968) 22:171–174.

(List continued on next page.)

Primary Examiner—Charles E. Cooley
Assistant Examiner—David Sorkin
(74) Attorney, Agent, or Firm—Roylance, Abrams, Berdo & Goodman, L.L.P.

(57) ABSTRACT

A float is used for preparing a density gradient in a parallel-walled vessel. The float has an outer peripheral surface that has a diameter smaller than an inner diameter of an inner surface of the vessel. With the float placed inside the vessel a liquid is introduced onto the float such that the liquid flows around the float between the float and the inner wall of the vessel. The shape and configuration of the float slows the velocity of the liquid such that there is only laminar flow as the liquid contacts other liquid below the float. Elimination of turbulent flow prevents mixing of different liquid introduced into the same vessel thereby forming layers of fluid. Preferably, the vessel is a centrifuge tube. In one embodiment, the outer diameter of the float is large enough to cause capillary action between the float and the inner surface of the centrifuge tube to force liquid to remain between the float and the inner surface of the centrifuge tube.

7 Claims, 5 Drawing Sheets

OTHER PUBLICATIONS

Clark et al., Hydrostatically Balanced Gradient–Formers: Programming of Gradients. *Anal Biochem* (1980) 103:94–100.

Coombs et al., Generating Sucrose Gradients in Three Minutes by Tilted Tube Rotation. *Anal Biochem* (1985) 148:254–259.

Corless JM., Simple and Inexpensive Fabrication of Small–Volume Density Gradients. *Anal Biochem* (1978) 84:251–255.

Gordon et al., A Simple Design of an Apparatus for the Generation of Sucrose Gradients for Large–Scale Zonal Separation of Ribosomal Subunits. *Anal Biochem* (1977) 83:763–766.

Gropper et al., Band–Forming Caps for the Layering of Sample in Swinging–Bucket Rotors. *Anal Biochem* (1966) 16:171–176.

Henderson AR., A Constant–Volume Device for Preparing Isokinetic Sucrose Density Gradients. *Anal Biochem* (1969) 27:315–318.

Hopkins TR., Another Density Gradient Fractionator. *Anal Biochem* (1973) 53:339–341.

Lange et al., A Semiautomated System for the Production and Analysis of Sucrose Density Gradients. *Anal Biochem* (1974) 59:129–145.

Leif RC., Density Gradient System: I. Formation and Fractionation of Density Gradients *Anal Biochem* (1968) 25:271–282.

Liedtke et al., An Apparatus for Density Gradient Forming and Nonpuncturing Fractionation. *Anal Biochem* (1974) 62:377–385.

Luthe DS., A Simple Technique for the Preparation and Storage of Sucrose Gradients. *Anal Biochem* (1983) 135:230–232.

Margolis J., A Versatile Gradient–Generating Device. *Anal Biochem* (1969) 27:319–322.

McRee D., Inexpensive Apparatus for Preparation of Multiple Discontinuous Gradient. *Anal Biochem* (1978) 87:648–652.

Neff et al., A Modified Fixed–Volume Mixer for Extended Sucrose Density Gradients. *Anal Biochem* (1971) 41:365–371.

Olenick et al., A Floating Device to Permit Fractionation of Density Gradients From the Top. *Anal Biochem* (1979) 97:72–76.

Samis HV., A Simple Density Gradient Generator. *Anal Biochem* (1966) 15:355–357.

Sartory et al., Design of a Generalized n–Solate Mixing–Chamber Gradient Generator. *Anal Biochem* (1978) 88:539–551.

Shearer G., A Syringe–Based Gradient Former for Linear and Exponential Gradients. *Anal Biochem* (1994) 221:397–400.

Sheeler et al., Method and Apparatus for Producing and Collecting a Multiplicity of Density Gradients. *Anal Biochem* (1978) 87:612–621.

Siakotos et al., New Loading System for Preparing Density Gradients for Swinging–Bucket Rotors Using Programmed Gradient Pumps. *Anal Biochem* (1971) 43:32–41.

Wallach DFH., A Simple System for Rapid Generation of Duplicate Density Gradients. *Anal Biochem* (1970) 37:138–141.

* cited by examiner

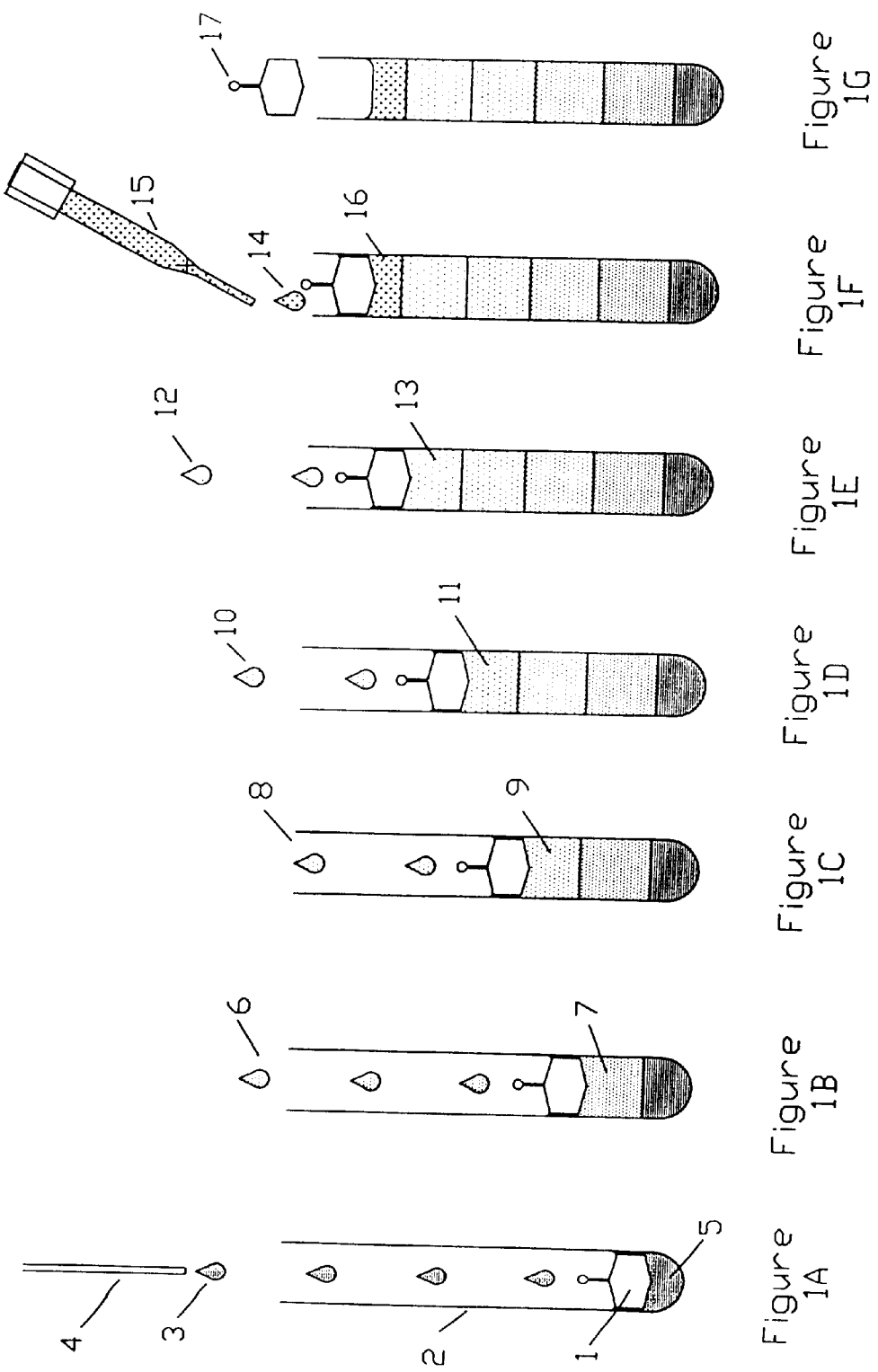

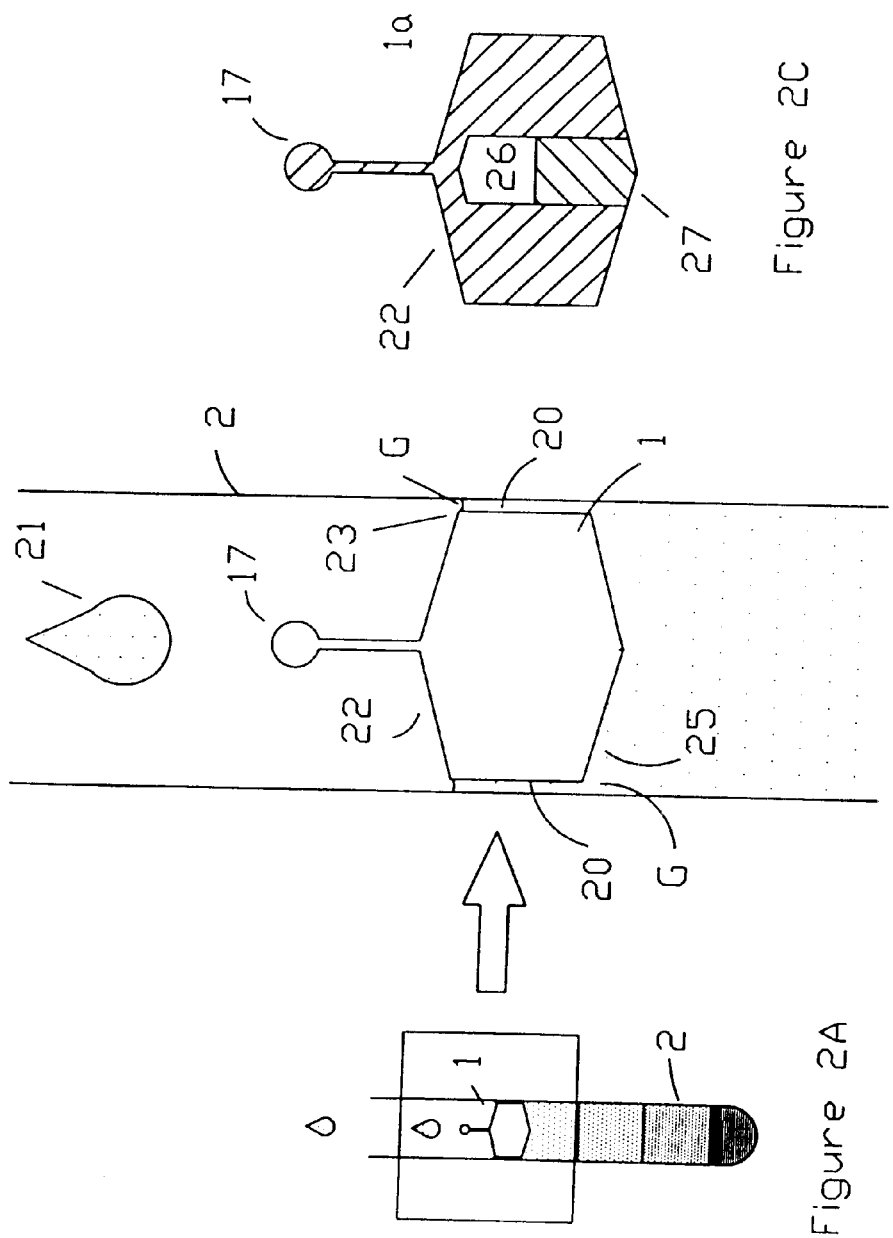

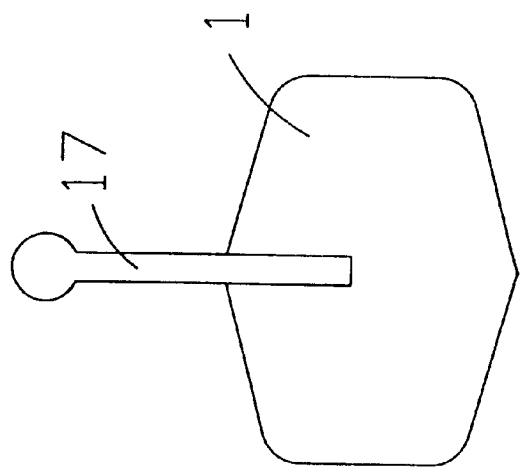
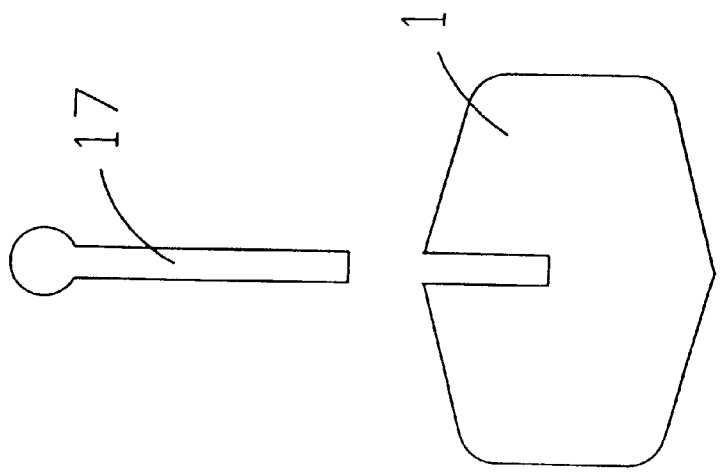

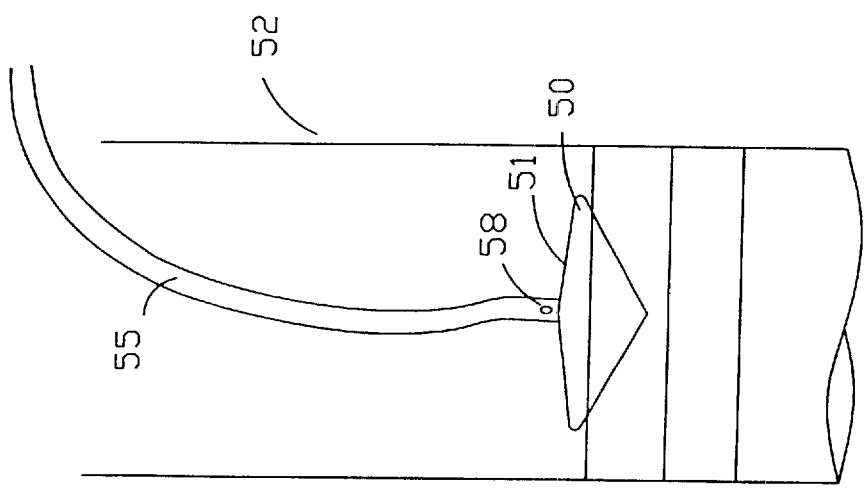

METHOD FOR MAKING DENSITY GRADIENTS

This application is a divisional of U.S. patent application Ser. No. 09/551,314, filed Apr. 18, 2000, now abandoned.

BACKGROUND OF THE INVENTION

A. Field of the Invention

The present invention relates to an apparatus and method for making a multiple density layers or gradients of fluid in a vessel in a highly reproducible manner using a float that floats on the surface of the fluid within the vessel.

B. Description of the Related Art

There are various fields where it is desirable to have density layers or gradients of fluid within a vessel for such purposes as the separation of matter, determining density, etc. Such density layers include, for example, a solution retained in a vessel where the fluid is divided into a plurality of layers, each layer having differing concentrations of a soluble material or solute. For example, a bottom or first layer of fluid may have a concentration of a solute that is X moles per liter; a second layer immediately above the first layer may have a concentration of 0.8X moles per liter; a third layer above the second layer may have a concentration of 0.6X moles per liter; and a fourth layer having a concentration of 0.4X moles per liter.

Liquids having gradients of temperature, concentration, density and color have been previously prepared. Liquid density gradients have been used for many years, for a wide variety of purposes, in a number of different industries. The inventor has numerous publications and patents regarding certain aspects of gradient formation and use including Anderson, N. G. Mechanical device for producing density gradients in liquids. Rev. Sci. Instr. 26: 891–892, 1955; Anderson, N. G., Bond, H. E., and Canning, R. E. Analytical techniques for cell fractions. I. Simplified gradient elution programming. Anal. Biochem. 3: 472–478, 1962; Anderson, N. G., and Rutenberg, E. Analytical techniques for cell fractions. A simple gradient-forming apparatus. Anal. Biochem. 21: 259–265, 1967; Candler, E. L., Nunley, C. E., and Anderson, N. G. Analytical techniques for cell fractions. VI. Multiple gradient-distributing rotor (B—XXI). Anal. Biochem. 21: 253–258, 1967.

A variety of other methods for making density gradients have been developed, and Bock, R. M. and Ling, N.-S., Anal. Chem. 26, 1543, 1954, and Morris, C.J.O.R, and Morris, P., Separation Methods in Biochemistry, Pitman Publishing, 2nd ed. (1976) have reviewed many of these. Only one of these methods allowed gradients to be made from multiple solutions, each having a different combination of reagents (Anderson, et al, "Analytical Techniques for Cell Fractions. I. Simplified Gradient Elution Programming", *Analytical Biochemistry* 3: 472–478, 1962) More recent innovations include the use of pumps and pistons, which are differentially controlled by microprocessors, e.g., the Angelique gradient maker (Large Scale Proteomics Corp. Rockville, Md.). Gradients may also be generated during high speed centrifugation by sedimenting a gradient solute such as cesium chloride or an iodinated x-ray contrast medium such as iodixanol. Gradients may be initially prepared as step gradients and linearized by diffusion, by gentle mixing, or by freezing and thawing. A list of references covering existing methods follows.

Density gradients are used to make two basic types of separations. The first separates particles on the basis of sedimentation rate (rate-zonal centrifugation), in which case particles are separated on the basis of the size and density (and to a lesser extent shape) and particles will sediment farther if centrifuged for a longer period of time. The second separates particles on the basis of isopycnic banding density, in which case particles reach their equilibrium density level, and do not sediment farther with continued centrifugation.

Four types of gradients are in general use with either of these basic methods. The first includes step gradients, made by layering a series of solutions of decreasing density (if the solutions are introduced one above the other), and of increasing density (if the solutions are introduced sequentially to the bottom of the tube). The second type comprises linear continuous gradients usually made by a mechanical gradient maker. These are usually introduced slowly through small tubing to the bottom of the centrifuge tube. Linear gradients for either rate zonal or isopycnic zonal centrifugation are useful for resolving very heterogeneous mixtures of particles.

The third type of gradient is non-linear, and may be designed to separate particles having a very wide range of sizes or densities. Non-linear gradient may be designed to separate particles on the basis of both sedimentation rate and isopycnic banding density in the same gradient, in which case some particles reach their isopycnic level at some point in the gradient, while others are still sedimenting. Generally such combined separations involve larger and denser particles which band near the bottom of the gradient, while other smaller, and usually lighter particles are still sedimenting in the upper portion of the gradient.

The fourth type of gradient is generated in a high centrifugal field by sedimentation of the major gradient solute, and is usually used for isopycnic banding.

Many reasons exist for desiring to control gradient shape. Gradient capacity (i.e., the mass of particles which can exist in a zone without causing a density inversion) is a function of gradient slope, and a steep gradient can support a greater mass of particles per unit gradient length than can shallow gradients. The greatest particle mass concentration in a gradient separation usually occurs immediately beneath the sample zone shortly after centrifugation is started. As different particles separate in the length of the gradient, the possibility of an overloaded zone diminishes. For this reason it is desirable to have a short steep gradient section immediately under the sample zone, where the highest gradient capacity is required.

An additional reason for desiring to control gradient shape is that when a population of particles is present that differ little in sedimentation rate, these can best be separated by sedimentation through a longer shallower section of the gradient. Such shallow sections are usually near the center of a gradient.

In the majority of density gradient separations, the gradients and their chemical composition are designed to optimize the separation of one or a few particles types. This accounts for the very large number of different gradient recipes that have been published for subcellular fractionation. Those used for the isolation of mitochondria, for example, are usually quite different from those used to isolate nuclei. For example, traces of divalent cations are required to control nuclear swelling, whereas such ions are generally deleterious to other subcellular particles. Low concentrations of nonionic detergents remove cytoplasmic contamination from nuclei, but are deleterious to the endoplasmic reticulum. Hence there has been no one procedure or gradient that has been optimized for the systematic separation of the majority of all subcellular particles. There is a need for reproducible means for including in gradients zones containing salts, detergents, enzymes and other reactive substances that would increase the number of different subcellular particles separated in one gradient.

Density gradient separations are important in proteomics research. High resolution two-dimensional electrophoresis (2DE) is widely used to produce global maps of the proteins in extracts prepared by solubilizing whole cells or tissues. By careful control of the procedures employed, use of staining procedures which are quantitative, and computerized image analysis and data reduction, quantitative differences in the abundance of individual proteins of ±15% has been achieved (Anderson, N. Leigh, Nance, Sharron L., Tollaksen, Sandra L., Giere, Frederic A., and Anderson, Norman G., Quantitative reproducibility of measurements from Coomassie Blue-stained two-dimensional gels: Analysis of mouse liver protein patterns and a comparison of BALB/c and C57 strains. Electrophoresis 6: 592–599, 1985; Anderson, N. Leigh, Hofmann, Jean-Paul, Gemmell, Anne, and Taylor, John, Global approaches to quantitative analysis of gene-expression patterns observed by use of two-dimensional gel electrophoresis. Clin. Chem. 30: 2031–2036, 1984). There is a need for precision subcellular fractionation that will allow changes in abundance of minor proteins to be accurately detected and measured in data which sums the abundance of all proteins found in all of the fractions of one sample.

This technology allows changes in gene expression, as reflected in protein abundance, to be studied under a wide range of conditions, and has led to the development of databases of protein abundance changes in response to a wide variety of drugs, toxic agents, disease states. In such studies large sets of data must be acquired and intercompared. Hence all stages in one pharmaceutical study, for example, must be standardized for intercomparability.

2DE maps of whole cells or tissues typically contain a thousand or more protein spots in sufficient abundance to allow each protein to be analyzed by mass spectrometry and identified and characterized. However, it is known that a very much larger number of proteins are actually present in tissue samples analyzed than are actually observed. The number present varies with cell or tissue type, and is believed to be up to ten or twenty times the number detected.

Different subcellular particles and the soluble fraction of the cell (the cytosol) contain many location-specific proteins which constitute only trace fractions of the total cell protein mass. Hence the total number of proteins resolved from one cell type or tissue could be greatly increased if the 2DE analysis were done on cell fractions rather than on whole cell or tissue extracts as has previously been demonstrated (Anderson, N. L., Giere, F. A., et al, Affects of toxic agents at the protein level: Quantitative measurements of 213 mouse liver proteins following xenobiotic treatment. Fundamental and Appl. Tox. 8: 39–50, 1987). If a drug effect study is to be done on cell fractions, however, the fractionation procedures must be quantitative, in the sense that the same organelles, or even mixtures of organelles are used in all analyses to be intercompared. There exists, therefore, an emerging need for high resolution density gradient separations using precision gradients in proteomics research. Making precision gradients reproducibly and in parallel has proven to be difficult, particularly when the gradients are shallow.

The protein composition of tissues such as liver varies diurnally, hence all the tissues from one group of animals are prepared at the same time of day, and, to be comparable, must be fractionated in parallel, on the same time schedule, and, if gradients are to be used, in identical gradients. Further, gradient fraction recovery must also be done from all gradients in parallel, under identical conditions. If the initial separations are done partly or entirely on a sedimentation rate basis, and if the recovered fractions are to then each be isopycnically banded, as is done in two-dimensional or s-ρ fractionation, then these subsequent steps must also be carried out in parallel. This, in turn, requires that the gradients be made in parallel.

Precision gradients are difficult to make in practice, and it is further difficult to confirm that a set of gradients are all identical without destroying them for analysis. Existing swinging bucket rotors generally allow six gradients to be centrifuged simultaneously. Larger numbers may be centrifuged if the lower resolution of vertical or near vertical tube rotors is accepted. Therefore if existing density gradient formers are to be used, a set of six or more of them operating in parallel will be required.

With any gradient maker, small amounts of turbulence or non-laminar flow typically cause solutions of differing concentrations to at least partially mix, thereby reducing the effectiveness and usefulness of the density layers. There is therefore a need for a method for decelerating fluids flowing into a tube, and for moving them slowly into position to form distinct bands.

One of many uses of density layers and gradients is in the fields of cell separation, sub-cellular fractionation and analysis, and density gradient methods are used in molecular biology and in polymer chemistry. Little attention has been paid to forming sets of precision-made gradients that are highly reproducible for cell separation. There is therefore a requirement for precision gradients adapted to cell separation.

One high resolution system is disclosed in "Development of Zonal Centrifuges", by N. G. Anderson, National Cancer Inst. Monograph 21, 1966) and employs zonal centrifuge rotors. The rotors are of high capacity, and process one sample at a time. However, the rotor volumes are too high for many applications. Angle head or vertical rotor tubes may also be employed (Sheeler, P., Centrifugation in Biology and Medicine, Wiley Interscience, N.Y., 1981, 269pp) using either step or continuous gradients. However these do not provide the resolution obtained with swinging bucket rotors.

There has been no reliable method for reproducibly locating and recovering organelle zones purely on the basis of the physical parameters of sedimentation rate and isopycnic banding density. Mathematical analyses, based on analysis not only of the biological particles separated, but of the gradients themselves have been required. These have been tedious and idiosyncratic to the rotors and conditions employed. The basic problem in preparing density gradients in tubes is that the liquid volume elements of either step (layers), or continuous gradients must be introduced into tubes very slowly or mixing will occur. This problem is only partially overcome by introducing the gradient into a set of tubes in an angle-head rotor during rotation.

Methods for producing one or a few gradients in parallel have been developed, but fraction recovery is generally done one at a time. The gradients are rarely identical, and it is difficult to introduce the sample layer on top of the gradient without mixing. Hence there is no published data on the quantitative high-resolution protein analysis of cell fractions of animals subject to various experimental treatments. If multiple, parallel identical gradients are to be prepared using gradient engines (for instance, see "Mechanical device for producing density gradients in liquids" by N. G. Anderson, Rev. Sci. Instruments 26: 891–892, 1955) one must have one machine for each tube being filled. Centrifugal gradient distributing heads have been built (see "A Method For Rapid Fractionation of Particulate Systems by Gradient Differential Centrifugation" by J. F. Albright, and N. G. Anderson, Exptl. Cell Research 15: 271–281, 1958), however the gradients actually produced tend to be uneven, and a refrigerated centrifuge is required. There is, therefore, a continuing need for simple gradient makers that produce identical gradients in parallel in sufficient number to satisfy current requirements. There is a further need for a simple, disposable and easily sterilizable system for making reproducibly sharp step gradients. An additional need exists for a system or device that can produce very narrow-step density gradients in which diffusion can rapidly and reproducibly even out the steps. A further need exists for a system or device which allows individual gradient steps to be rapidly pipetted into centrifuge tubes, either manually or robotically, and in which the introduced fluid does not disturb the underlying gradient. A still further need exists for a gradient making device in which the composition of the successive layers, while forming a stable density series, differ in composition relative to salts, enzymes, detergents or other reactive materials.

SUMMARY OF THE INVENTION

One object of the present invention is to provide a rapid, simple and reproducible method and apparatus for forming a multiplicity of liquid density gradients in vessels.

Another object of the present invention is to provide a rapid, simple and reproducible method and apparatus for forming a multiplicity of liquid density gradients in vessels for rate-zonal separations, for isopycnic banding separations, or a combination of the two.

Yet another object of the present invention is to provide an apparatus and method for reproducibly producing a plurality of liquid density gradients in a plurality of corresponding vessels, each vessel having a specific predetermined liquid density gradient.

An additional object of the present invention is to provide means for making liquid density gradients in which aliquots of a liquid density series are rapidly pipetted into the centrifuge tubes without regard to potential stirring or mixing.

A further object of the invention is to decelerate the aliquots ejected from pipettes or automatic pipetters, and to cause them to flow evenly into position without disturbing the underlying fluids.

A further object of the invention is to provide means for making the linear or complex gradients by making them initially as step gradients having very small density differences per step.

A further object of the present invention is to produce step gradients in which the steps are so small that diffusion rapidly evens out the gradient.

A still further object of the present invention is to make the gradient making components disposable and easily sterilizable.

It is a further object of the present invention to make possible construction of sets of identical gradients in a short period of time.

It is an additional object of the present invention to make possible addition of the sample layer on top of the gradient at any time after the gradient is formed.

In accordance with one aspect of the present invention, there is a method for producing liquid density gradients in a vessel using a float within the vessel includes the steps of:

inserting the float in the vessel;

introducing a first liquid into the vessel;

introducing a second liquid into the vessel such that the second liquid contacts at least one surface of the float upon entering the vessel, contact between surfaces of the float and the second liquid allowing the second liquid to form a layer above the first liquid thereby forming separate layers of liquid; and repeating the second introducing step with successive introducing steps with a third, fourth and so on liquid.

The float used in the above method slows the velocity of fluid such that flow of liquid is laminar thereby limiting mixing of the two liquids.

In accordance with another aspect of the present invention, an apparatus for producing liquid density gradients includes a vessel and a float positionable in the vessel. The float is formed with at least one surface that is shaped to inhibit acceleration of fluid introduced into the vessel thereby restricting turbulent flow of the fluid.

An outer peripheral surface of the float and the inner surface of the vessel are sized such that in response to fluid being introduced into the vessel above the float, the fluid undergoes capillary action moving downward beneath the float in the vessel.

BRIEF DESCRIPTION OF THE DRAWINGS

Further advantages of the disclosed invention will become apparent from a reading of the following description when read in conjunction with the accompanying drawings where like reference numerals are used to identify like parts, in which:

FIGS. 1A, 1B, 1C, 1D, 1E, 1F, and 1G are side views of a vessel and a float for producing a density gradient in the vessel in accordance with the present invention;

FIGS. 2A, 2B and 2C show details of the design and operation of float;

FIGS. 4A and 4B are a side view showing yet another embodiment of the float; and FIG. 5 is a side view showing still another embodiment of the float.

DETAILED DESCRIPTION OF THE INVENTION

Figure 3C:
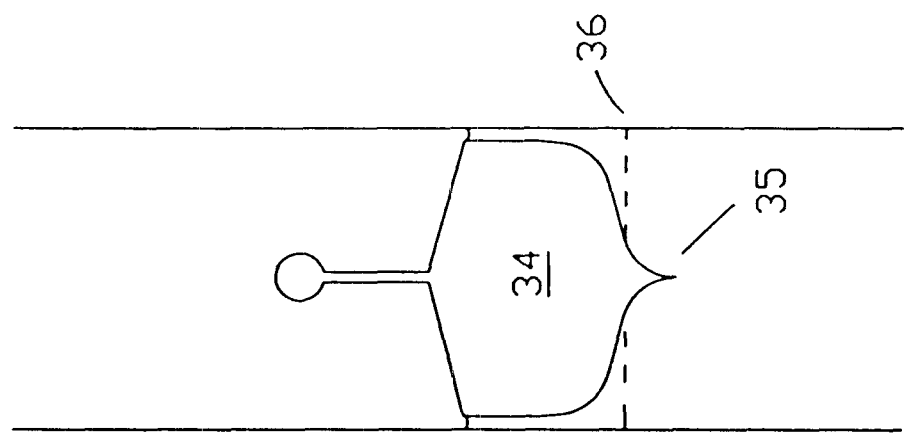
FIGS. 3A, 3B and 3C are side views showing alternate embodiments of the float.

A first embodiment of the present invention is illustrated in FIGS. 1A, 1B, 1C, 1D, 1E, 1F, and 1G. In accordance with the present invention, a float 1 is used to form a step gradient within a vessel 2, as depicted in FIGS. 1A, 1B, 1C, 1D, 1E, 1F, and 1G. However, it should be understood that the float 1 may also be used to create a continuous gradient (not shown) where a density gradient is introduced gradually, and continuously changes along the height of the vessel. In FIG. 1A the float 1 in the vessel 2 rises and floats on top of a liquid 3 introduced from a source 4. The diameter of the float 1 in the first embodiment is preferably slightly smaller than the inside diameter of the vessel 2.

The introduced liquid 3 contacts and then flows around the float 1, passes down between the outer surface of the float 1 and the inner surface of the vessel 2 and, as shown in FIG. 1A, produces a first zone 5. Typically, the zone 5 has the highest density of all the layers or zones, as is described in greater detail below. As shown in FIG. 1B, a second liquid 6 is introduced in a similar manner to produce zone 7. As shown in FIGS. 1C, 1D, and 1E, the procedure is repeated with succeeding less dense liquids 8, 10, and 12, to produce zones 9, 11, and 13.

A sample 14 to be analyzed within the vessel 2 is introduced last from a pipette 15 to produce zone 16 as shown in FIGS. 1F and 1G. Finally as shown in FIG. 1G, the float 1 is removed by grasping a projecting pin 17 and lifting. The vessel 2 depicted in FIG. 1G with sample and gradient may then be subjected to treatment by, for instance, insertion into a swinging bucket rotor of a centrifuge device. When a continuous gradient is required, the step gradient is prepared beforehand, and diffusion for a determined period of time used to convert the step gradient into a continuous one.

FIGS. 2A, 2B and 2C illustrate details of the float 1 and basic principles of operation of the float within the vessel 2. The float 1 and vessel 2 depicted in FIG. 2A is shown enlarged in FIG. 2B. The float 1 has an outer peripheral surface 20 that is shaped to conform to an inner surface of the vessel 2. For instance, the vessel 2 shown in the drawings is a tube having a circular cross-section when viewed from top or bottom. The float 1 has a corresponding circular shape with the outer peripheral surface 20 having a diameter that is smaller than the inner diameter of the surface of the vessel 2. Therefore, a gap G having a predetermined width is defined between the outer peripheral surface 20 of the float 1 and the inner surface of the vessel 2. The gap G may vary in size depending upon the solutions to be introduced into the vessel 2 and the relative sizes of the float 1 and vessel 2.

In the depicted embodiment, the gap G is relatively small such that surface tension of the solution produces a capillary action within the gap G to maintain liquid in the gap and to prevent air bubbles in the gap. In many applications of the present invention the viscosity of fluid in the gap is sufficient to eliminate the possibility of turbulent fluid flow within the vessel 2 as the solution exits the gap and moves around the float 1. Therefore, mixing of layers of solution under the gap is almost non-existent and very sharp boundaries are produced between the zones, even with very small density increments.

It should be understood that diminished rate of fluid flow is a desirable result of the present invention depicted in FIGS. 1A–1G and FIGS. 2A–2C. The actual size of the gap G may be varied according to the viscosity of the liquids used and the size of the vessel 2. However, although capillary action and restricted rate of fluid flow are important to the present invention, it is possible to use the float 1 of the present invention without capillary action. For instance, the shape of the surfaces of the float 1 may be formed to discourage any increases in velocity of fluid moving over the surfaces of the float 1 to avoid turbulent flow of the fluids entering the vessel 2. The shape and surface contours of the float 1 are such that the flow of solution around the float 1 as the solution moves downward into the vessel 2 is minimal. Specifically, a upper surface 22 of the float 1 is tapered having a conical shape such that as fluid contacts the upper surface 22 viscous flow slows fluid motion as the fluid approaches an edge 23 of the float 1.

It should be understood that the upper surface 22 may have a more rounded shape when viewed from the side and need not be conical in shape so long as sufficient surface area is provided to allow the adhesive forces of the fluid to make contact with the upper surface 22 to slow movement of the fluid.

It should also be understood that the vessel 2 and float 1 may have any of a variety of shapes when viewed in cross-section. The depicted vessel 2 is a tube having a circular cross-section. The vessel 2 may also have a square or triangular cross-sectional shape and the float 1 a corresponding square or triangular cross-sectional shape.

As shown in FIG. 2B, when a droplet 21 of solution is dropped from above the float 1, the droplet 21 is distributed circumferentially on upper tapered surface 22 and moves toward the edge 23, where the solution flows evenly into the gap G, and thereafter slowly moves on to the upper surface of the underlying layer of liquid. Velocity or speed of flow of the solution is also further decelerated as it flows around lower taper 25. Capillary forces and solution viscosity are sufficient to keep the velocity of the solution in the gap G to a minimum and further, regardless of the density of the liquids used, the gap G typically remains filled with solution due to the capillary action.

The float 1 is also formed with an upper integral pin 17 that allows the float 1 to be inserted and removed easily from the vessel 2. The density of the float 1 itself may be dictated by the choice of construction material or, as shown in FIG. 2C, an alternate embodiment of a float 1a may be formed with a cavity 26 sealed by plug 27 to adjustably control the density of the float 1. The floats 1 and 1a are preferentially constructed of polypropylene which has a density of approximately 0.95 g/cc, and the pin 17, being a small fraction of the mass of the float, may be either integrally molded into the float and of the same material, or may be another material such as polycarbonate or other plastic, and be inserted in a hole in the float as shown in FIGS. 4A and 4B. Further, the density of the float may be adjusted by inserting pins 17 having a variety of weights. For instance, a plurality of pins 17 may be produced, each pin 17 having a different mass for selectively adjusting the overall weight of the float.

Figure 3B:
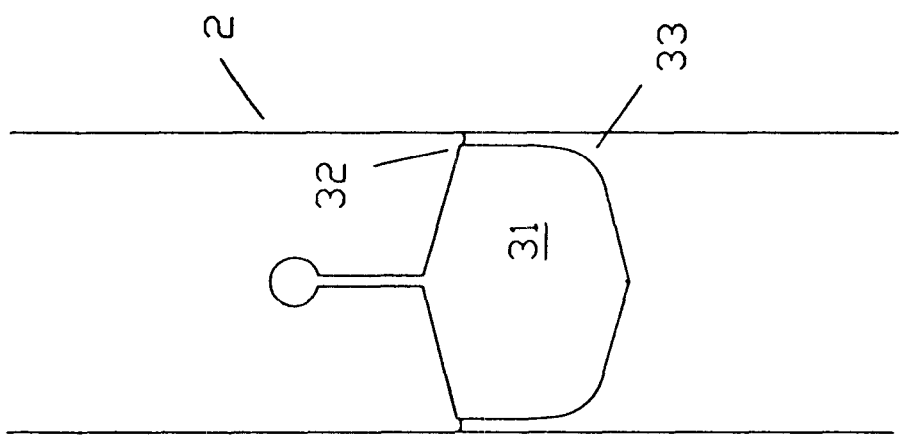
Figure 3A:
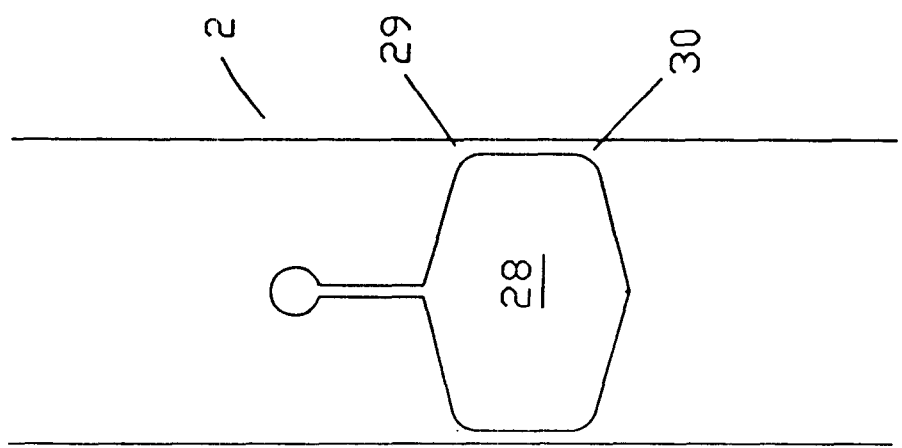

The shape of the various surfaces of the float 1 is not limited to the depictions in FIGS. 1A–1G and FIGS. 2A–2C. FIGS. 3A, 3B and 3C illustrate alternative float designs. In FIG. 3A a float 28 has upper edges 29 and lower edges 30 rounded to further assist in slowly accelerating flow at the upper edge, and decelerating flow at the lower edge as liquid flows over the underlying liquid. In FIG. 3B float 31 has different upper edge 32 and lower edge 33, with the upper edge 32 sharp to help prevent air bubbles between the float and tube 2, and the lower edge 33 well rounded, while in FIG. 3C float 34 has a tip 35 extended to further control flow around the float. The shape of the lower surface of the float 34 and the tip 35 assist in keeping the interface 36 between two steps in the gradient sharp.

The inventors have tested and designed floats for Beckman Ultraclear tubes for the Beckman SW41 Ti rotor and for polycarbonate tubes for the Beckman SW28 rotor. For the SW 41 tubes, the floats were constructed of solid polypropylene, 13.1 mm in diameter with top and bottom tapers of 15 degrees, and were 6.35 mm high measured at the edge. Wall clearance was 0.25 mm (gap G). For the SW 28 rotor tubes, long and short versions of the floats were constructed which were 10.5 mm and 6 mm high at the edge, had clearances of 1 and 0.6 mm, with 15 degree tapers at the top and bottom. Holes through the float had 1.6 mm internal diameters, and the pins were made of 0.9 mm outside diameter polycarbonate monofilament. After the pins were inserted, one end was melted in a reducing flame to produce a ball at the tip, while the other end was heated to produce a small enlargement, which, when put into the float, sealed the pin in place.

All radial clearances kept the gap G between the float and the centrifuge tube wall (vessel 2) full of liquid at all densities used. Occasionally when floats were dropped into dry tubes, they became stuck at the bottom, hence the "round" at the bottom of the centrifuge tube is preferably filled with a "cushion", i.e., densest gradient solution used, initially.

Experimentally it was found that if the first 4–5 drops (circa 0.1 ml) of the solution being added were introduced slowly over a period of 5–10 seconds, extraordinarily sharp interfaces were produced below the float. The remainder of the gradient step could then be introduced more rapidly. Sharp interfaces were produced with the density difference between two steps being as little as 0.0017 g/ml.

The use of floats allows gradients to be formed as a series of short well defined zones that may be arranged to be linear, sigmoidal, or of other gradient shape. If required, the gradients can then be evened by diffusion. The float/vessel arrangement allows the production of gradients that are more reproducible than those produced by conventional gradient makers, and allows many gradients to be made in parallel without requiring a multiplicity of gradient makers.

However, it should also be understood that by using the float of the present invention, it is possible to quickly pour an amount of a fluid directly onto the top of the float and the fluid will gradually seep down around the float to create a layer fluid without significantly disturbing the layer or layers of fluid already beneath the float. Without the float, pouring of fluid into the vessel with previously introduced fluid layers in the vessel would guarantee mixing of the layers thereby making gradient layer formation impossible. Therefore, one important result possible by using any of the above described embodiments of the present invention is that a density gradient can be produced quickly and reproducibly without concern of the rate of flow of any one liquid onto the upper surface of the float.

In yet another embodiment of the present invention depicted in FIG. 5, a float 50 is positioned in a vessel 52 with the vessel 52 having an inner diameter that is significantly greater than the outer diameter of the float 50. The float 50 is similar to the float described above in FIGS. 1A–1G, but has a tube 55 attached to an upper surface of the float 50. The tube 55 is hollow and includes several apertures 58 for allowing the flow of fluid from within the tube 55 to an upper surface of the float 50. As fluid is introduced from the tube 55 via the apertures 58, the fluid contacts the upper surface of the float 50 and flows along the upper surface due to adhesion thereby slowly entering the vessel. Adhesion between the surfaces of the float 50 and the fluid slows velocity of the fluid such that the fluid forms a well defined layer above previously introduced layers.

The upper surface 51 of the float 50 is preferably formed with only a slight incline to further inhibit acceleration of the fluid. The tube 55 attached to the fluid may also be used to raise and lower the float 50 with respect to the vessel 52. Specifically, a mechanical arm may be attached to the tube 55 to remotely control movement of the float in and out of the vessel 51. It should be understood that the tube 55 is flexible to allow movement of the float 50 upward as the vessel 52 is filled with fluid.

A fluid flow controller (not shown) is preferably used with the embodiment of the float 50 to control the amount of fluid introduced for each desired layer.

It should be understood that gradients may be used in many applications outside of the field of molecular biology. For instance, a vessel having a plurality of layers solution, each layer having a different density due to a specific concentration of solute in each layer, may be used determine the density of an unknown material. A sample of material of unknown density dropped into the vessel will settle in the layer having a like density thereby providing a means for determining density of the unknown material. For example, different classes of plastics have different densities. Small pieces of plastic may easily be tested by dropping one small sample into a vessel having a plurality of solutions, each solution having a predetermined density such that the plurality of layers define a stepped density gradient. The plastic particle will drop to a layer having the same density and will float above those layers having a heavier density. Similarly, identification of a gemstone based on density can be conducted.

The materials and methods of the instant invention can be used in the separation of cellular elements from samples of whole blood, blood products or diluted blood. For example, white blood cells can be obtained from blood by density gradient centrifugation. Suitable materials to effect separation of the cellular elements and particularly the nucleated cellular elements from blood include media that comprise colloidal silica, silica gel, sugars, such as sucrose, ficoll, and particular products such as Ficoll-Hypaque, Isopaque, LymphoPrep and Percoll. See, for example, Parish et al., Eur. J. Imm. (1974) 4:808.

Generally single step gradients are produced by gently layering the blood cell suspension onto a high density medium. The preparation then is centrifuged at low speed to effect separation of the cells.

Alternatively, the blood cell suspension can be layered onto a linear gradient, for example; of bovine serum albumin prior to centrifugation. The blood cell suspension can be layered onto a discontinuous gradient, for example, of bovine serum albumin. The densities of the layers can be configured so that the various elements band at the interfaces of the layers.

To ensure that discrete, sharp layers and hence tight banding of cells occurs, it is beneficial to ensure a sharp interface between the cell suspension, for example, blood, and the separation medium. That goal can be achieved with use of an apparatus of interest. A suitably sized float of interest is used. The float of interest rests atop the separation medium. The float of interest allows passage of the, for example, blood along the lateral sides thereof and along the inner surface of the centrifuge tube containing the medium, float and cell suspension with minimal turbulence to ensure formation of a discrete linear interface of cell suspension and separation medium.

REFERENCES

Anderson, N. G., ed. The Development of Zonal Centrifuges. National Cancer Institute Monograph 21, 1966, 256 pp,.

Price, C. A. Centrifugation in Density Gradients. Academic Press, N.Y. 1982 430 pp.

Scheeler, P. Centrifugation in Biology and Medical Science. John Wiley & Sons N.Y. 1981 269 pp.

Anderson, N. G. A simple method for observing refractive index gradients in liquids. Biochim. Biophys. Acta 25: 418, 1957

Albright, J. F., and Anderson, N. G. A method for the rapid fractionation of particulate systems by gradient differential centrifugation. Exptl. Cell Research 15: 271–1181, 1958

Anderson, N. G., Bond, H. E., and Canning, R. E. Analytical techniques for cell fractions. I. Simplified gradient elution programming. Anal. Biochem. 3: 472–478, 1962.

Fisher, W. D., G. B. Cline, and Anderson, N. G. Density gradient centrifugation in angle-head rotors. The Physiologist. 6: 179, 1963.

Anderson, N. G., and Rutenberg, E. Analytical techniques for cell fractions. A simple gradient-forming apparatus. Anal. Biochem. 21: 259–265, 1967.

Candler, E. L., Nunley, C. E., and Anderson, N. G. Analytical techniques for cell fractions. VI. Multiple gradient-distributing rotor (B—XX). Anal. Biochem. 21: 253–258, 1967

Luthe DS A simple technique for the preparation and storage of sucrose gradients. In: Anal Biochem 135:230–2, 1983 Hirst W, Cox RA A method for predicting the location of particles sedimenting in sucrose gradients. Anal Biochem 131:51–68, 1983

Clark AG, Gellen JW Hydrostatically balanced gradient-formers: programming of gradients. Anal Biochem 103:94–100, 1980

Olenick JG, Lorenz PE A floating device to permit fractionation of density gradients from the top. Anal Biochem 97:72–6, 1979

Sartory WK, Halsall HB Design of a generalized n-solute mixing-chamber gradient generator. In: Anal Biochem 88:539–51, 1978

McRee D Inexpensive apparatus for preparation of multiple discontinuous gradient. In: Anal Biochem 87:638–52, 1978

Sheeler P, Doolittle MH, White HR Method and apparatus for producing and collecting a multiplicity of density gradients. Anal Biochem 87:612–21, 1978

Michov BM A concentration gradient system. Anal Biochem 86:432–42, 1978

Corless JM Simple and inexpensive fabrication of small-volume density gradients. Anal Biochem 84:251–5, 1978

Gordon J, Ramjoue HP A simple design of an apparatus for the generation of sucrose gradients for large-scale zonal separation of ribosomal subunits. Anal Biochem 83:763–6, 1977

Gregor HD A new method for the rapid separation of cell organelles. Anal Biochem 82:255–7, 1977

Khandjian EW In situ studies of subcellular particles immobilized in sucrose-acrylamide density gradients. Anal Biochem 77:387–96 1977

Allington RW, Brakke MK, Nelson JW, Aron CG, Larkins BA Optimum conditions for high-resolution gradient analysis. Anal Biochem., 73:78–92, 1976

Gasser KW, DiDomenico J, Hopfer U Separation of cell organelles in density gradients based on their permeability characteristics. Anal Biochem 171:41–6, 1988

Shearer G Jr A syringe-based gradient former for linear and exponential gradients. In: Anal Biochem., 221:397–400, 1994

Graham J, Ford T, Rickwood D The preparation of subcellular organelles from mouse liver in self-generated gradients of iodixanol. Anal Biochem 220:367–73, 1994

Ford T, Graham J, Rickwood D Iodixanol: a nonionic iso-osmotic centrifugation medium for the formation of self-generated gradients.: Anal Biochem 220:360–6, 1994

Davis PB, Pearson CK Characterization of density gradients prepared-by freezing and thawing a sucrose solution. Anal Biochem 91:343–9, 1978

Liedtke R, Mosebach KO An apparatus for density gradient forming and nonpuncturing fractionation. Anal Biochem 62:377–85, 1974

McCarty KS Jr, Vollmer RT, McCarty KS Improved computer program data for the resolution and fractionation of macromolecules by isokinetic sucrose density gradient sedimentation. Anal Biochem 61:165–83, 1974

Lange CS, Liberman DF A semiautomated system for the production and analysis of sucrose density gradients. Anal Biochem 59:129–45, 1974

Bylund DB, Bruening G Prediction of centrifugation times for equilibrium and velocity sedimentation on various gradients. Anal Biochem 58:47–56, 1974

Sinclair JH Churchill L, Banker G, Cotman CW Gradient design to optimize rate zonal separations. Anal Biochem 56:370–82, 1973.

Hopkins TR Another density gradient fractionator. Anal Biochem 53:339–41, 1973

Atherton RS, Hawtin P, Hutchinson P Chromatography and zonal centrifugation. Prediction of the optimum initial chamber compositions of a multichambered concentration and density gradient device. Anal Biochem 49:326–35, 1972

Dingman CW A convenient program for the rapid calculation of sedimentation coefficients in linear salt or sucrose gradients. Anal Biochem., 49:124–33, 1972

Leifer W, Kreuzer T Experiments and theoretical calculations for forming gradients for zonal rotor centrifugation. Anal Biochem 44:89–96, 1971

Siakotos AN, Pennington K, McInnes A New loading system for preparing density gradients for swinging-bucket rotors using programmed gradient pumps. In: Anal Biochem 43:32–41, 1971

Neff SH, Meeker GL A modified fixed-volume mixer for extended sucrose density gradients. Anal Biochem 41:365–71, 1971

Pretlow TG Estimation of experimental conditions that permit cell separations by velocity sedimentation on isokinetic gradients of Ficoll in tissue culture medium. Anal Biochem 41:248–55, 1971

Wallach DF A simple system for rapid generation of duplicate density gradients. Anal Biochem 37:138–41, 1970

Shore SL, Phillips DJ, Reimer CB Preformed frozen sucrose gradients—a new laboratory aid. Anal Biochem 31:114–7, 1969

Margolis J A versatile gradient-generating device. Anal Biochem., 27:319–22, 1969

Henderson AR A constant-volume device for preparing isokinetic sucrose density gradients. Anal Biochem 27:315–8, 1969.

Leif RC Density gradient system. II. A 50 channel programmable undulating diaphragm peristaltic pump. Anal Biochem 25:283–96,1968

Leif RC Density gradient system. I. Formation and fractionation of density gradients. Anal Biochem 25:271–82, 68

Ayad SR, Bonsall RW, Hunt S A simple method for the production of accurate linear gradients using a constant-speed peristaltic pump. Anal Biochem 22:533–5, 1968.

Mach O, Lacko L Density gradient in a dextran medium. Anal Biochem 22:393–7, 1968

McCarty KS, Stafford D, Brown O Resolution and fractionation of macromolecules by isokinetic sucrose density gradient sedimentation. Anal Biochem 24:314–29, 1968

Birnie GD, Harvey DR A simple density-gradient engine for loading large-capacity zonal ultracentrifuge rotors. Anal Biochem 22:171–4, 1968

Anderson NG, Rutenberg E Analytical techniques for cell fractions. VII. A simple gradient-forming apparatus. Anal Biochem 21:259–65, 1967

Candler EL, Nunley CE, Anderson NG Analytical techniques for cell fractions. VI. Multiple gradient-distributing rotor (B—XXI).: Anal Biochem 21:253–8, 1967

McEwen CR Tables for estimating sedimentation through linear concentration gradients of sucrose solution. Anal Biochem 20:114–49, 1967

Gropper L, Griffith O Band-forming caps for the layering of sample in swinging-bucket rotors. Anal Biochem 16:171–6, 1966

Samis HV Jr A simple density gradient generator. Anal Biochem 15:355–7, 1966

Camacho-Vanegas O, Loreni F, Amaldi F., Flat absorbance background for sucrose gradients. Anal Biochem 228:172–3,1995.

Smith GD, Osterloh KR, Peters TJ Computational analysis of density gradient distribution profiles. Anal Biochem 160:17–23, 1987

Morand JN, Kent C A one-step technique for the subcellular fractionation of total cell homogenates. Anal Biochem 159:157–62, 1986

Coombs DH, Watts NR Generating sucrose gradients in three minutes by tilted tube rotation.: Anal Biochem 148:254–9, 1985.

Samuels S., A continuous density gradient apparatus for use in zonal ultracentrifuges. Anal. Biochem. 41:164–7, 1964.

Anderson, N. Leigh, Nance, Sharron L., Tollaksen, Sandra L., Giere, Frederic A., and Anderson, Norman G., Quantitative reproducibility of measurements from Coomassie Blue-stained two-dimensional gels: Analysis of mouse liver protein patterns and a comparison of BALB/c and C57 strains. Electrophoresis 6: 592–599, 1985.

Anderson, N. Leigh, Hofmann, Jean-Paul, Gemmell, Anne, and Taylor, John, Global approaches to quantitative analysis of gene-expression patterns observed by use of two-dimensional gel electrophoresis. Clin. Chem. 30: 2031–2036, 1984.

Anderson, N. L., Giere, F. A., Nance, S. L., Gemmell, A., Tollaksen, S. L., and Anderson, N. G. Effects of toxic agents at the protein level: Quantitative measurement of 213 mouse liver proteins following xenobiotic treatment. Fund. Appl. Tox., 8: 39–50, 198

All references cited herein are herein incorporated by reference in entirety.

Although the present invention has been described with reference to the preferred embodiments, the invention is not limited to the details thereof. Various substitutions and modifications will occur to those of ordinary skill in the art and all such substitutions and modifications are intended to fall within the scope of the invention as defined in the appended claims.

What is claimed is:

1. A method for isolating nucleated cells from blood comprising;

(a) introducing a blood sample into a vessel containing blood cell separating medium and a float being formed with at least one surface that is shaped to inhibit acceleration of a blood sample introduced into said vessel, thereby restricting turbulent flow of said blood sample onto said separating medium;

(b) allowing said float to rise to the top of said sample and for said blood sample to contact said blood cell separating medium; and (c) centrifuging said sample in said vessel to produce a gradient, wherein nucleated cells separate and form a discrete layer in said gradient and wherein the orientation and position of said at least one surface in said vessel is effected by parallel sides perpendicular to said surface.

2. A method of separating nucleated cells from a sample comprising blood, comprising:

(a) introducing a blood separation medium into a vessel with parallel walls;

(b) inserting a float into said vessel, wherein said float has a shape that conforms to an inner surface of said vessel with a space therebetween;

(c) introducing said sample into said vessel onto an upper exposed surface of said float and allowing the sample to pass by said float as said float floats, wherein said space enables said sample to pass by said float to form without turbulence a layer having an interface with said medium;

(d) removing said float or allowing said float to stay on top of said sample until after centrifugation and then removing said float;

(e) centrifuging said vessel; and (f) removing nucleated cells of blood contained in a layer at or about said interface.

3. The method of claim 2, wherein an outer peripheral surface of said float and an inner opposing surface of said vessel have a round shape.

4. The method of claim 2, wherein step (b) is preformed prior to step (a).

5. The method of claim 2, wherein said medium comprises silica.

6. The method of claim 2, wherein said medium comprises a copolymer of sucrose and epichlorohydrin.

7. The method of claim 2, wherein said sample is diluted prior to step (c).

* * * * *